United States Patent
Jain et al.

(10) Patent No.: US 8,389,018 B2
(45) Date of Patent: Mar. 5, 2013

(54) NANO/MACROPOROUS BIOACTIVE GLASSES MADE BY MELT-QUENCH METHODS

(76) Inventors: Himanshu Jain, Bethlehem, PA (US); Hassan Mohamady Mohamed Moawad, Bethlehem, PA (US)

(*) Notice: Subject to any disclaimer, the term of this patent is extended or adjusted under 35 U.S.C. 154(b) by 494 days.

(21) Appl. No.: 12/526,599

(22) PCT Filed: Feb. 13, 2008

(86) PCT No.: PCT/US2008/053851
§ 371 (c)(1),
(2), (4) Date: Aug. 10, 2009

(87) PCT Pub. No.: WO2008/101011
PCT Pub. Date: Aug. 21, 2008

(65) Prior Publication Data
US 2010/0015244 A1    Jan. 21, 2010

Related U.S. Application Data

(60) Provisional application No. 60/889,659, filed on Feb. 13, 2007.

(51) Int. Cl.
*A01N 59/26* (2006.01)
*A61K 33/42* (2006.01)
(52) U.S. Cl. ...................................... 424/602
(58) Field of Classification Search .................. 424/602
See application file for complete search history.

(56) References Cited

U.S. PATENT DOCUMENTS

| 4,749,665 A | 6/1988 | Yano et al. |
| 5,336,642 A | 8/1994 | Wolcott |
| 6,993,406 B1 | 1/2006 | Cesarano, III et al. |
| 2007/0203584 A1 | 8/2007 | Bandyopadhyay et al. |

FOREIGN PATENT DOCUMENTS

WO    2008101011 A1    8/2008

OTHER PUBLICATIONS

Spierings, G.A.C.M., J Materials Sci 28: 6261-6273 (1993), "Wet chemical etching of silicate glasses in hydrofluoric acid based solutions."*
Hosano et al., J Am Ceram Soc 72: 1587-1590 (1989).*
Navarro et al., Biomaterials 25: 4233-4241 (2004).*
International Search Report and Written Opinion from PCT/US2008/053851 by Jain et al. (Jun. 25, 2008).
Coelho et al., J. Biomed. Mater. Res. B 75(2), 451-56 (2005).

(Continued)

*Primary Examiner* — James H. Alstrum-Acevedo
*Assistant Examiner* — Thor Nielsen
(74) *Attorney, Agent, or Firm* — Rhoads & Sinon LLP; Kurt L. Ehreiman

(57) ABSTRACT

The methods and materials described herein provide novel and simple procedures for the preparation of nano/macroporous glasses, in which the pore structure is characterized by interconnected pores of, e.g. both hundreds of micrometers and several to tens of nanometers in size. Such materials may be used for enhanced bone regeneration, bioscaffolds, drug delivery devices, and filtration media, among other uses. For example, silica-based bone tissue scaffolds are made with a controlled nano/macroporosity, which enhances bone regeneration performance. Also provided herein are new biocompatible $CaO$—$Na_2O$—$P_2O_5$—$SiO_2$ glasses prepared by thermal melt-quench methods that result in spinodal phase separation and crystallization of phases at very different length scales. Selective chemical leaching of these phases causes formation of interconnected multi-modal porosity, with pore sizes ranging from several nanometers to tens of micrometers.

13 Claims, 10 Drawing Sheets

OTHER PUBLICATIONS

Yan et al., Biomaterials 27(18), 3396-403 (Jun. 2006).

Hench, Splinter, Allen, et al; Bonding Mechanisms at the Interface of Ceramic Prosthetic Materials; J Biomed. Mater. Res. Symposium; No. 2 (Part 1) (pp. 117-141); 1971, USA.

Kityk, Imiolek, Majchrowski, Michalski, et al; Photoinduced second harmonic generation in partially crystallized $BiB_3O_6$ glass; Optics Communications 219 (2003) 421-426; 2003, Poland.

Shinzato, Nakamura, Ando, Kokubo, Kitamura, et al; Mechanical properties and osteoconductivity of new bioactive composites consisting of partially crystallized glass beads and poly (methyl methacrylate); pp. 557-563; 2002, Japan.

Basu, Nagendra, Li, Ramamurty, et al; Microstructure and mechanical properties of partially crystallized La-based bulk metallic glass; Philosophical Magazine; 83:15, 1747-1960, India, Singapore.

Mastelaro, Zanotto, et al; Anisotropic residual stresses in partially crystallized $Li_2O-2SIO_2$ glass ceramics; Journal of Non-Crystalline Solids 247; pp. 79-86, 1999, Brazil.

Gilbert, Ritchie, et al; Fracture toughness and fatigue-crack propagation in a Zr-Ti-Cu-Be bulk metallic glass; pp. 476-478; 1997, California, USA.

Incoccia, Mobilio, et al; Structural Investigations of $TiO_2-SiO_2$ Glassy and Glass-Ceramic Material Prepared by the Sol-Gel Method; Journal of Non-Crystalline Solids 74 (1985); pp. 129-146; Italy.

* cited by examiner

NANO/MACROPOROUS BIOACTIVE GLASSES MADE BY MELT-QUENCH METHODS

CROSS-REFERENCE TO RELATED APPLICATIONS

This application claims the priority of U.S. patent application No. 60/889,659, filed Feb. 13, 2007, which is incorporated herein by reference in its entirety.

STATEMENT REGARDING FEDERALLY SPONSORED RESEARCH OR DEVELOPMENT.

This subject matter is related to work conducted at least in part with financial support from the United States National Science Foundation International Materials Institute for New Functionality in Glass (DMR-0409588) and Materials World Network (DMR-0602975) programs. The government of the United States may have certain rights herein.

FIELD

This disclosure pertains to nano/macroporous bioactive glass materials made by melt-quench methods and uses thereof, e.g. as bone tissue scaffolds for use in regenerative medicine.

BACKGROUND

One of the great challenges of the 21$^{st}$ Century is increasing life expectancy, while at the same time maintaining quality of life in an aging population. Regenerative medicine is, therefore, a new strategy that seeks to repair damaged or diseased tissues to their original state or function. For example, regenerative medicine seeks to help natural healing processes to work faster by using special materials with human cell cultures, often referred to as "scaffolds" or "bioscaffolds," which act as three-dimensional templates for cell growth and differentiation and formation of living tissues.

Synthetic scaffolds have been proposed as a new means of tissue reconstruction and repair. Scaffolds belong to a new generation of biomedical structures, which rely on the concept of regeneration of diseased or damaged tissue to its original state or function. In contrast, current clinical methods are based on replacement by implantation or transplantation. Current clinical methods such as implantation or transplantation possess well-known drawbacks. Those drawbacks include, for example, lack of ability to self-repair, limited vascularization of implants, limited number of donors, and possibility of rejection of transplanted tissues.

Scaffolds serve as both a physical support and as an adhesive substrate for isolated cells, during in vitro culturing and subsequent in vivo implantation. Scaffolds may be used to deliver cells to desired sites in the body, to define a potential space for engineered tissue, and/or to guide the process of tissue development. Cell transplantation on scaffolds has been explored for the regeneration of skin, nerve, liver, and pancreas tissues using various biological and synthetic materials. In particular, scaffolds containing dual porosity at the nanoscale and macroscale have been alleged to exhibit better performance in terms of crystallization of hydroxycarbonate apatite, cell adhesion and proliferation, and vascularization. Known materials, however, lack sufficient mechanical strength to be of practical use or lack an interconnected pore morphology that is compatible with vascularization.

Accordingly, a continuing and unmet need exists for new and improved synthetic bioactive tissue scaffolds, scaffold materials, as well as for methods for fabricating scaffolds having interconnected multi-modal porosity. A further need exists for bioactive and biocompatible glass systems (such as soda-lime phosphosilicates), including glasses having morphology and textures that enable formation of a bonelike hydroxyapatite layer.

SUMMARY

The methods and materials described herein provide novel materials and methods for providing glass-based bioactive porous tissue scaffolds, having a novel, biocompatible pore structure, characterized by interconnected pores of, e.g. both hundreds of micrometers and several to tens of nanometers in size. These methods and materials are useful for providing enhanced bone regeneration and performance. The glass-based bone tissue scaffolds are characterized by controlled nano/macroporosity, which enhances bone regeneration and performance.

Also provided herein are new biocompatible materials, e.g. $CaO$—$Na_2O$—$P_2O_5$—$SiO_2$ glasses, prepared by melt-quench methods characterized by spinodal phase separation followed by crystallization of phases at very different length scales. Selective and controlled chemical leaching of these phases causes formation of interconnected multi-modal porosity, (with "multi-modal" being defined herein as characterized by pore sizes ranging from several nanometers (nanoporus) to tens or hundreds of micrometers). Such novel nano/macroporous glasses (i.e., glasses with both nanopores and macropores) have application by way of non-limiting example as superior tissue bioscaffolds.

By way of non-limiting example, an improved 24.5CaO-(27.5-x)$Na_2O$-6$P_2O_5$-(42+x)$SiO_2$ (wt %) (with x=0-10) bioactive glass series is provided by introducing engineered multi-modal porosity in bulk samples. Such glasses may be prepared by melt-quench methods to yield an amorphous phase-separated microstructure that varies with $SiO_2$ fraction. For the ranges of about 42% to about 43% and about 50% to about 52 wt % $SiO_2$, the phase separation occurs by nucleation and growth, giving two disconnected phases. The glasses containing about 44% to about 49 wt % $SiO_2$ show interconnected structure typical of spinodal decomposition. The degree of interconnectivity of the amorphous phases depends on the thermal history. Heat treatment produces two main crystalline phases of sodium calcium silicates, viz. $Na_2Ca_2Si_3O_9$ and $Na_2CaSi_3O_8$. Additional calcium silicate ($CaSiO_3$) and calcium phosphate ($Ca_4P_6O_{19}$) phases may also be present. Immersion of samples in a simulated body fluid ("SBF") shows that the formation of hydroxyapatite on the surface is significantly higher in the heat treated samples. Controlled leaching in aqueous acid (e.g., 1N HCl) introduces multi-modal nano/macroporosity, which improves their usefulness as bone scaffolds.

Such scaffolds may be used in tissue engineering and regeneration techniques, in stimulating cell growth and differentiation, as well as in the formation of tissues. Methods of use may include the harvesting and culture of stem cells from a patient on the scaffold in vitro, thereby creating a tissue/scaffold biocomposite that can be implanted in a selected target site (e.g., in a human or animal in need thereof), further uses may provide tissue regeneration occurring at the rate at which the scaffold resorbs.

The synthetic methods described herein allow for the preparation of bone tissue scaffolds with a controlled multi-modal porosity that is characterized by interconnected macropores above the minimum pore size required for tissue in-growth and eventual vascularization (e.g., approximately 100 µm in size). The interconnected, coral-like multi-modal porosity (e.g., nanoporosity and macroporosity) is achieved without significantly attenuating the strength of the material.

Additional features may be understood by referring to the accompanying drawings, which should be read in conjunction with the following detailed description and examples.

DETAILED DESCRIPTION

Figure 1:
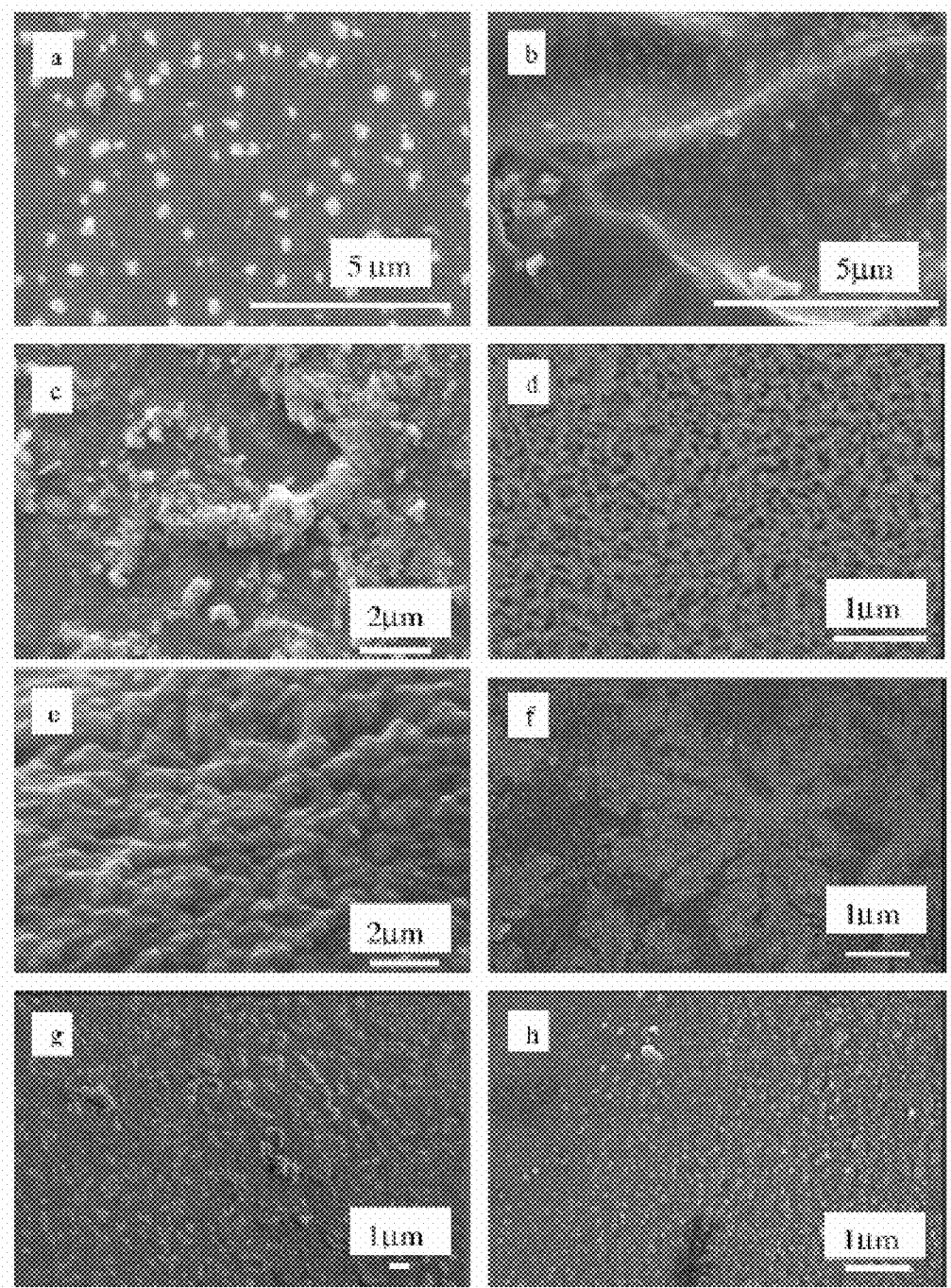
FIG. 1 illustrates SEM micrographs showing binodal and spinodal phases separation in various glass samples in accordance with an example embodiment hereof: (a) 42S, (b) 43S, (c) 44S, (d) 45S, (e) 46S, (f) 49S, (g) 50S, and (h) 52S.

Bioactive glasses and glass-ceramics have been widely studied during the past three decades after Hench et al. reported that some silicate glasses within the $Na_2O$—CaO—$P_2O_5$—$SiO_2$ system chemically bond with living bone. L. L. Hench, R. J. Splinter, W. C. Allen, and T. K. Greenle, "Bonding Mechanisms at the Interface of Ceramic Prosthetic Materials," *J. Biomed. Mater. Res.* 5, 117-41 (1971). The so-called "45S" glass of composition $24.5Na_2O$-$24.5CaO$-$6P_2O_5$-$45SiO_2$ (in wt %) is perhaps the most widely investigated material within this bioactive glass system. For example, 45S is non-toxic, biocompatible, and clinically used for middle-ear prostheses. C. Wang, T. Kasuga, and M. Nogami, "Macroporous Calcium Phosphate Glass-Ceramic Prepared by Two-Step Pressing Technique and Using Sucrose as a Pore Former," *J. Mater. Sci.: Mater. Med.* 16, 739-44 (2005). Subsequently, it was shown that 45S glass bonds with bone better if it is porous. F. Balas, D. Acros, J. Perez-Pariente, and M. Vallet-Regi, "Textural Properties of $SiO_2$—CaO—$P_2O_5$ Glasses," *J. Mater. Res.* 16, 1345-48 (2001). There has also been increasing interest in the fabrication of biocompatible glass having interconnected porosity. See, for example, P. Sepulveda, J. R. Jones, and L. L. Hench, "Bioactive Sol-Gel Foams for Tissue Repair," *J. Biomed. Mater. Res.* 59, 340-48 (2002); A. R. Boccaccini and V. Maquet, "Bioresorbable and Bioactive Polymer/Bioglass Composites with Tailored Pore Structure for Tissue Engineering Applications," *Comp. Sci. Tech.* 63, 2417-29 (2003).

The sol-gel process is the most widely used method for introducing porosity into biocompatible glass. Glass obtained by known sol-gel processes is initially porous on the nanoscale. P. Sepulveda, J. R. Jones, and L. L. Hench, "Characterization of Melt-Derived 45S5 and Sol-Gel-Derived 58S Bioactive Glasses," *J. Biomed. Mater. Res.* 58, 734 (2001). Sepulveda et al. studied the difference in the physical properties of the melt-derived 45S and sol-gel-derived 58S ($60SiO_2$:$36CaO$:$4P_2O_5$ in mol %) glass powders with various particle sizes. They concluded that the sol-gel-derived glass with a nanoporous texture (pore size 6-9 nm) and a large surface area possessed higher bioactivity and osteogenic potential than the 45S glass having a low porosity and surface area. S. J. Gregg and K. S. W. Sing, Adsorption, Surface Area and Porosity, $2^{nd}$ edition, p. 25, Academic Press, London, 1982. For purposes of this application, pores are classified as "nanopores" if the average pore diameter is <100 nm and "macropores" if the average pore diameter is >10 µm. Of course, "nanopores" and "macropores" are not intended to be mutually exclusive, and the nano/macroporous materials described herein are multi-modal; that is, they are simultaneously nanoporous and macroporous.

On the other hand, independent of the benefits of nanoporous structure, bioactive glass with macroporosity (pore size >10 µm) provides better integration and vascularization of scaffold with osseous tissue. Therefore, a bioactive glass with multi-modal porosity provides an ideal texture for bone replacement or scaffold applications. Although the coexistence of nano- and macropores may be unstable under equilibrium conditions, very recently, Marques et al. have succeeded in using sol-gel methods to prepare biocompatible calcium silicate and calcium phosphosilicate glasses with pores of a few nanometers as well as larger than 100 µm in size. See, e.g. WO 2008/028036 (application number PCT/US2007/077238). In that case, sol-gel methods with an additional processing stage of polymerization-induced phase separation caused the creation of macroporosity while retaining nanoporosity. However, it remains challenging to produce sufficiently large samples by sol-gel methods because of high shrinkage and cracking during processing.

For fabricating porous glass, an alternative to the sol-gel approach is the classical Vycor® process in which a homogeneous glass prepared by the melt-quench method is heat treated to produce spinodal decomposition into two interconnected phases. Then, one phase is preferentially etched in a suitable acid, leaving behind glass with three-dimensional porosity. This method has been successfully used in making porous glasses with nearly uniform nanoscale porosity, using glass within the $Na_2O$—$B_2O_3$—$SiO_2$ series. See, e.g. A. K. Varshneya, Fundamentals of Inorganic Glasses, p. 66. Academic Press, New York, 1994.

In known sol-gel methods, interconnected nanoscale porosity in glass can be introduced. When the resulting materials are implanted in the human body, a bonelike hydroxyapatite ("HA") layer is formed on their surface. T. Peltola, M. Joinen, H. Rehiala, E. Levanen, J. B. Rosenholm, I. Kangasniemi and A. Yli-Urpo, "Calcium Phosphate Formation on Porous Sol-Gel-Derived $SiO_2$ and CaO—$P_2O_5$—$SiO_2$ Substrates in Vitro," *J. Biomed. Mater. Res.* 44, 12-21 (1999). The biocompatibility of such materials is easily established since the inorganic part of the human bone is a kind of calcium phosphate viz. HA. Hench et al. reported that there are some bioactive glasses that also bond to soft tissues through attachment of collagen to the glass surface. R. Li, A. E. Clark and L. L. Hench, "An Investigation of Bioactive Glass Powders by Sol-Gel Processing," *J. Appl. Biomater.* 2, 231-39 (1991); L. L. Hench and J. Wilson, "Bioceramic," *MRS Bull.* 16, 62-74 (1991); L. L. Hench, "Bioceramic: From Concept to Clinic," *J. Am. Ceram. Soc.* 74, 1487-510 (1991). A characteristic of those soft-tissue bonding compositions is a very rapid rate of HA formation. A common characteristic of bioactive glasses and bioactive glass-ceramics is a time-dependent modification of the surface that occurs upon implantation.

Soda-lime phosphosilicates may be used as bioactive glass because they promote strong bonding to bone tissue, while avoiding a foreign body (immune) response. The bone regeneration properties of soda-lime phosphosilicate bioactive glass are due to the presence of phosphorus and calcium. For melt-processed soda-lime phosphosilicate bioactive glasses, low silica content and a high calcia and soda content are typically required for the glass to have a high surface reactivity in an aqueous medium. The primary role of sodium ions in the bioactive glass is to facilitate the glass melting process. The dissolution of $Na^+$, $P^+$, and $Ca^{2+}$ from the glass in solution results in the formation of a silica-rich and a $CaO—P_2O_5$ rich layer. The latter layer promotes the formation of HA, which has a calcium to phosphorus ("Ca/P") ratio compatible with bone structure, which is believed to be necessary to promote tissue binding to the glass. C.-C. Lin, L.-C. Huang and P. Shen, "$Na_2CaSi_2O_6—P_2O_5$ Based Bioactive Glasses. Part 1: Elasticity and Structure," *J. Non-Cryst. Solids* 351, 3195-203 (2005).

In addition to the chemical composition that determines the bioactivity of soda-lime phosphosilicates, their particular morphologies and textures of the glass are important to permit bonding with tissue. Therefore, it is desirable to design soda-lime phosphosilicate bioactive glasses to provide porous scaffolds and articulating surfaces. An example scaffold material provided has the following characteristics: (a) an interconnected network of macroporosity to enable tissue in-growth and nutrient delivery to the center of the regenerated tissue, and (b) nanoporosity to promote adhesion. Their ideal characteristics have been accomplished using sol-gel methods. See, e.g. S. J. Gregg and K. S. W. Sing, "Adsorption, Surface Area and Porosity," p. 25, $2^{nd}$ ed., Academic Press, London, N.Y., 1982; N. Li, Q. Jie, S. Zhu and R. Wang, "Preparation and Characterization of Macroporous Sol-Gel Bioglass," *Ceram. Iternat.* 31, 641-46 (2005). However, multi-modal porosity has not heretofore been provided by melt-quench methods.

Accordingly, in an embodiment, a method of making a nano/macroporous material includes steps of providing a composition (or article of manufacture) including a phase-separated, partly crystallized glass and leaching it with a leaching solution (e.g., an acid or alkaline solution) to thereby produce a nano/macroporous material. A least a portion of the composition includes a phase-separated, partly crystallized glass.

In another embodiment, the method may include, prior to leaching, heating the composition to a temperature sufficient to convert at least a portion of the phase-separated glass to a ceramic.

For example, the phase-separated, partly crystallized glass may include $CaO—Na_2O—P_2O_5—SiO_2$. Similarly, the nano/macroporous material may be biocompatible.

In another embodiment, a biocompatible silica-based bioscaffold composition includes a melt-quenched, phase-separated, partly-crystallized glass characterized by the presence of multi-modal porosity formed by selective chemical leaching. Multi-modal porosity is characterized by an interconnected microstructure of nanopores and macropores. Generally, macropores have an average pore diameter of greater than about 10 micrometers, and nanopores have an average diameter of less than about 100 nanometers.

For example, a biocompatible silica-based bioscaffold composition may include a glass of the formula $24.5CaO-(27.5-x)Na_2O-6P_2O_5-(42+x)SiO_2$ (wt %), wherein x is from about 0 to about 10 (e.g., x is about 3). As a further example, a biocompatible silica-based bioscaffold composition may include a glass of the formula 24.4% $Na_2O$-26.9% CaO-2.6% $P_2O_5$-46.1% $SiO_2$ (mol %).

In another embodiment, a method of making a nano/macroporous $CaO—Na_2O—P_2O_5—SiO_2$ glass material includes steps of melting a mixture of $SiO_2$, $CaCO_3$, $NaCO_3$, and $Ca_5(OH)(PO_4)_3$ at a melting temperature for a first time period, annealing the mixture at a reduced temperature for a second time period, and thereafter leaching the mixture with a leaching solution to thereby produce a nano/macroporous glass material. Such a method may also include steps of heating the mixture to a nucleation temperature ($T_n$) for a third time period, and thereafter heating the product of the previous step to a crystal growth temperature ($T_x$) for a fourth time period.

In the foregoing example, the melting temperature may be about 1400° C. or greater (e.g., 1500° C.) and the first time period may be about 1 h or longer (e.g., 2 h). The reduced temperature may be about 500° C. (e.g., 520° C.) and the second time period may be about 1 h or longer. The nucleation temperature is generally about 670° C. and the third time period is typically about 1 h or longer. By way of further example, the crystal growth temperature may be about 700° C. to about 1100° C. (e.g., 750° C.). Similarly, the crystal growth temperature may be about 750° C. to about 1075° C. The fourth time period may be about 3 h or longer (e.g., the fourth time period may be about 6 h to about 9 h).

The leaching solution may be either acidic or basic in accordance with the principles described herein. An example leaching solution has a pH of less than 7 and comprises an inorganic mineral acid (e.g., the leaching solution is a 1N HCl solution). Typically, the leaching step is carried out for about 1 h in 1N HCl at about 85° C. using about 50 mL acid per gram of glass, although one skilled in the art will appreciate that the leaching step may be adapted to other materials based upon no more than routine experimentation.

The materials described herein have a variety of uses. For example, a method of inducing bone growth or regeneration in a mammal includes a step of implanting a biocompatible silica-based bioscaffold composition in a mammal in need thereof, such that hydroxycarbonate apatite growth occurs on an interior or exterior surface of the material. Likewise, a method of stimulating cell growth or differentiation comprising a step of placing one or more cells onto a surface of a biocompatible silica-based bioscaffold composition. Other uses for such nano/macroporous materials that will be readily appreciated in the art include use as filtration media (e.g., differential filtration), and as a drug delivery system in which a medicine leaches out of implanted material over long time periods (e.g., months to years), among other uses.

EXAMPLES

Example 1

The $24.5CaO-(27.5-x)Na_2O-6P_2O_5-(42+x)SiO_2$ (wt %) glass series (with x=0-10) was prepared with starting materials: $SiO_2$ (99.99% pure), $CaCO_3$ (99.95% pure), $Na_2CO_3$ (99.98% pure) and $Ca_5(OH)(PO_4)_3$ (99.99% pure). The $SiO_2$ content was varied within a controlled weight percentage between 42-52 wt % using 11 different values as listed in Table 1. The $P_2O_5$ wt %, CaO wt %, and Ca/P ratio were kept constant at 6 wt %, 24.5 wt % and 5.2 wt %, respectively. The individual batches were mixed and ground using an alumina mortar and pestle. Each batch was melted in a platinum crucible at 1500° C. Each homogenized melt was poured onto a stainless steel mold, and was then annealed to relax residual stresses. The result was a glass phase-separated by two quite different mechanisms: The first mechanism produced interconnected spinodal-like texture. The second mechanism led to disconnected, precipitated fine structure. To identify the glass samples described herein, we have followed the notation XXS proposed by Hench, where the first two letters represent the wt % of $SiO_2$, e.g. 42S means a glass that contains 42 wt % $SiO_2$. To indicate the transformation of a glass to glass-ceramic, we have modified the notation to XXSGY, where G signifies glass-ceramic and Y indicates a particular heat treatment.

TABLE 1

Temperature and time of heat treatment schedule of various glasses in the $24.5CaO—(27.5 - x)Na_2O—6P_2O_5—(42 + x)SiO_2$ (wt %) series (with x = 0 – 10).

| $SiO_2$ (wt. %) | Sample I.D. | Crystal Growth Step ($T_x$ for time t) |
|---|---|---|
| 42 | 42SG1 | 750° C. for 6 h |
| 43 | 43SG1 | 750° C. for 6 h |
| 44 | 44SG1 | 750° C. for 6 h |
| 45 | 45SG1 | 750° C. for 6 h |
| 46 | 46SG1 | 750° C. for 6 h |
| 47 | 47SG1 | 750° C. for 6 h |
| 48 | 48SG1 | 750° C. for 6 h |
| 49 | 49SG1 | 750° C. for 6 h |
| 50 | 50SG1 | 750° C. for 6 h |
| 52 | 52SG1 | 750° C. for 6 h |
| 45 | 45SG2 | 1075° C. for 6 h |
| 48 | 48SG2 | 1075° C. for 6 h |
| 49 | 49SG2 | 1075° C. for 6 h |
| 45 | 45SG3 | 750° C. for 9 h |

All samples were given the same nucleation heat treatment.

To induce additional multiple phase separation, each sample was further heat treated in two steps: (a) nucleation step at $T_n$, which included heating to 670° C. and holding there for a fixed time, and (b) crystal growth step at $T_x$, which included heating at the same rate to two different values of $T_x$ (750° C. or 1075° C.) and holding there for varying times. Table 1 describes the temperature and time of heat treatment schedule for various samples. To create nano/macroporosity in the prepared glasses, the heat treated glasses were then leached in 1N HCl for 1 h at 85° C. Other time periods were studied, but for this material 1 h appeared to be optimal.

To identify the multiple phases and microstructure, the samples were analyzed by X-ray diffraction technique ("XRD") and scanning electron microscopy ("SEM"). A Philips XL30 SEM was used to examine sectioned and polished samples of each glass to elucidate the phase separation and microstructure. The cross-section samples were coated with gold. The elemental distribution in different phases was analyzed with EDAX device equipped in the Hitachi 4300 Field Emission Scanning Electron Microscope. The pore size distribution of the samples was determined by mercury porosimeter (Micromeritics Auto Pore IV).

Selected samples were then tested for the biocompatibility and adhesion, formation of apatite layer was observed in vitro in simulated body fluid ("SBF") that contained inorganic ions in concentration corresponding to human blood plasma. The SBF was prepared by dissolving reagent grade NaCl, $NaHCO_3$, KCl, $K_2HPO_4.3H_2O$, $MgCl_2.6H_2O$, $CaCl_2.2H_2O$, and $Na_2SO_4$ in deionized water. The fluid was buffered at (physiological) pH 7.4 at 37° C. Ten glass and glass-ceramic ($T_n$ 670° C. for 1 h and $T_x$ for 750° C. for 6 h or 9 h) samples were used to investigate the reaction of soda-lime phoshosilicate samples with SBF. Each specimen (2 mg) was immersed in 1 mL of SBF contained in a polyethylene bottle covered with a tight lid for 20 h. The results are further discussed herein.

Referring to the accompanying drawings, FIG. 1 shows photomicrographs of the various structures and phases observed in the soda-lime phosphosilicate bioactive glass. The morphologies and mechanisms of phase separation varied in samples containing 42-52 wt % $SiO_2$. For $SiO_2$ in the 42-43 and 50-52 wt % ranges, the compositions produce fine structure consisting of disconnected precipitates, which we interpret as a consequence of the composition being in the binodal region. For $SiO_2$ in the 44-49 wt % range, the compositions produce interconnected spinodal texture.

Figure 2:
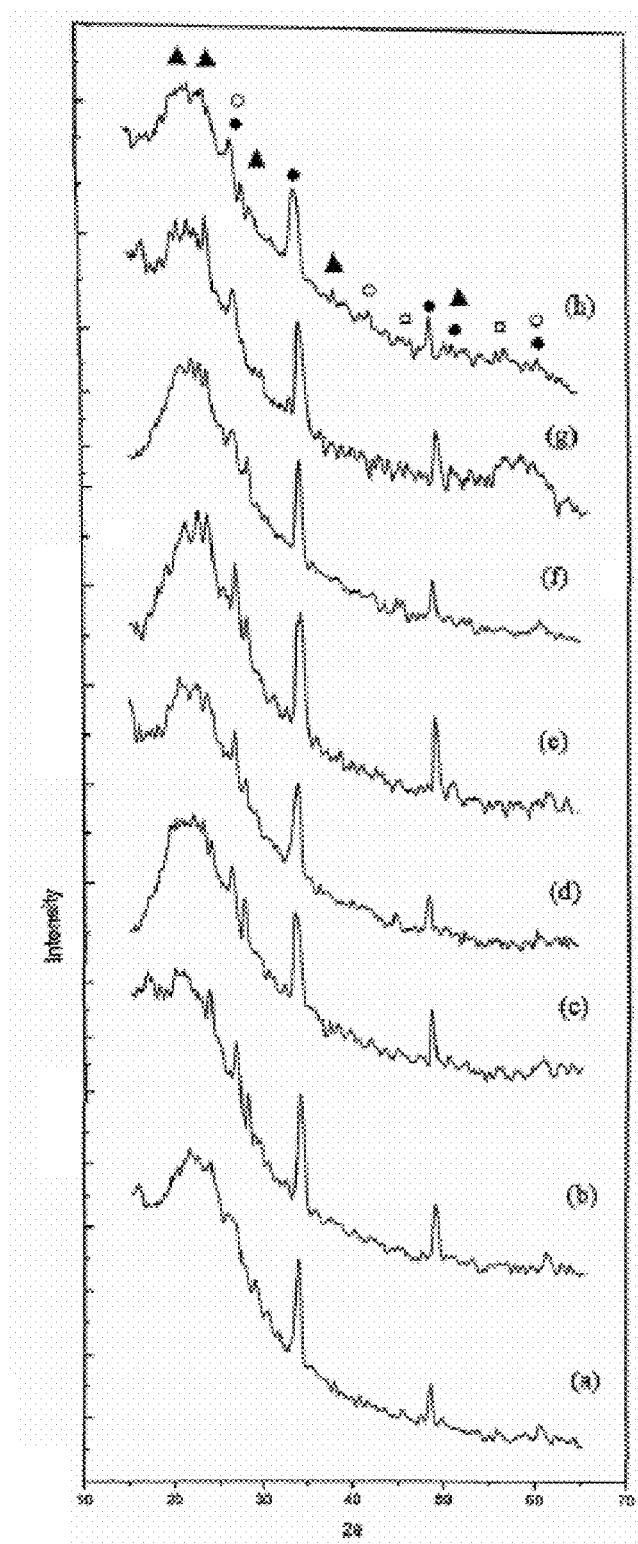
FIG. 2 illustrates X-ray diffraction patterns of glass-ceramic samples after crystallization heat treatments of previously phase-separated glasses: (a) 44SG1, (b) 45SG1, (c) 46SG1, (d) 47SG1, (e) 49SG1, (f) 45SG2, (g) 47SG2, and (h) 49SG2. [● $Na_2Ca_2Si_3O_9$; ○ $Na_2CaSi_3O_8$; ▲ $Ca_4P_6O_{19}$; and □ $CaSiO_3$].

The XRD pattern of the prepared bioactive glass samples, which were subjected to the two step heat treatment, is shown in FIG. 2. The crystal phases are identified as $Na_2Ca_2Si_3O_9$, $Na_2CaSi_3O_8$, $Ca_4P_6O_{19}$ and $CaSiO_3$ (Wollastonite). The location of diffraction peaks matches the standard powder diffraction file ("PDF") card numbers 1-1078, 12-671, 15-177 and 42-550, respectively. See O. P. Filho, G. P. LaTorre and L. L. Hench, "Effect of Crystallization on Apatite-Layer Formation of Bioactive Glass 45S5," *J. Biomed. Mater. Res.* 30, 509-14 (1996); O. Peitl, E. D. Zanotto and L. L. Hench, "Highly Bioactive $P_2O_5$—$Na_2O$—CaO—$SiO_2$ Glass-Ceramics," *J. Non-Cryst. Solids* 292, 115-26 (2001). The heat treatment of soda-lime phosphosilicate bioactive glasses resulted in coarsening of an already phase-separated glass structure and crystallization of these phases. In addition, it induced the formation of new crystalline phase, Wollastonite at high temperature 1075° C. (FIGS. 2(g) and 2(h)) similar to that found by De Aza et al. P. N. De Aza and Z. B. Luklinska, "Effect of glass-ceramic microstructure on its in vitro bioactivity," *J. Mater. Sci.: Mater. Med.* 14, 891-98 (2003).

Figure 3:
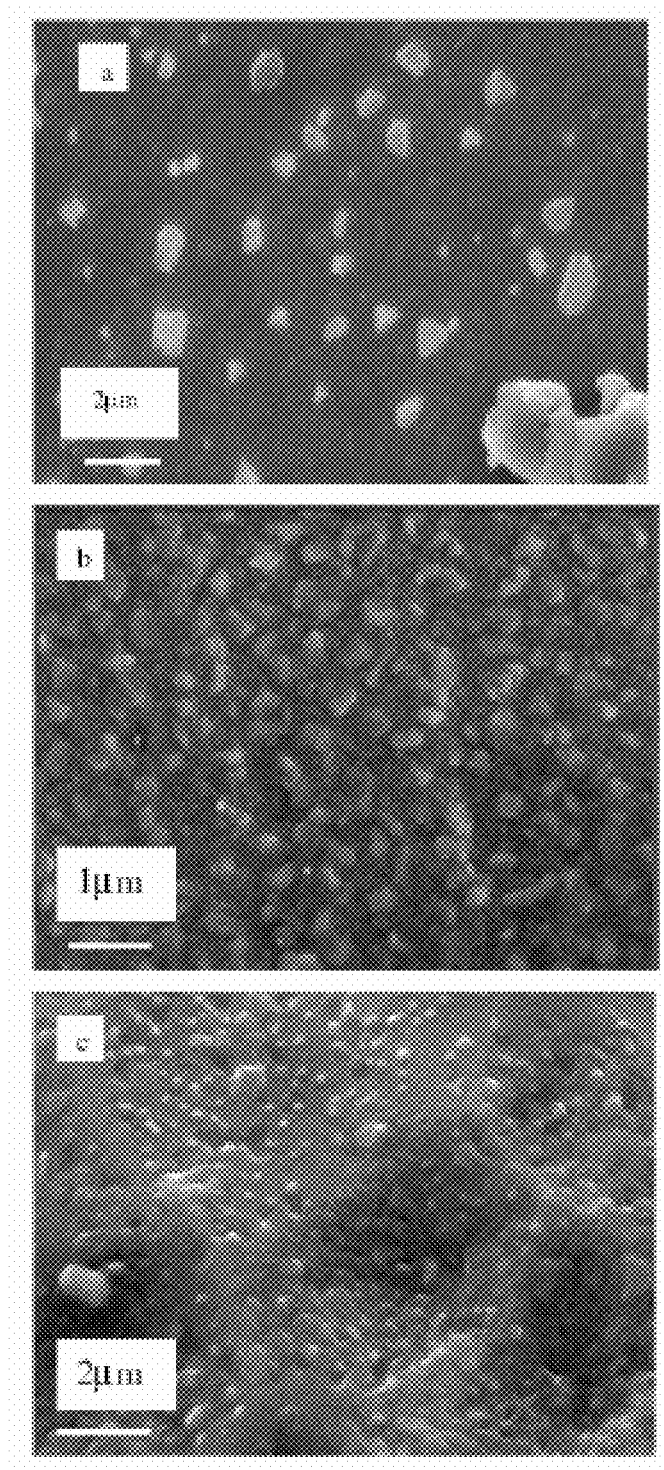
FIG. 3 illustrates SEM micrographs of glass-ceramic samples after the crystallization heat treatment: (a) 43SG1, (b) 45SG1, and (c) 49SG1.

FIG. 3 shows microstructure of 43SG1, 45SG1, and 49SG1 samples, which were subjected to crystallization heat treatment in two steps: (a) nucleation at 670° C., followed by (b) crystal growth at $T_x$, which included heating to 750° C. and holding there for 6 h. It is clear that the size of microphases increased with heat treatment. The structure of 43SG1, 45SG1, and 49SG1 glass-ceramic has coarsened. The silica-rich phase, instead of forming a continuous network, as in the sample shown in 43 S, FIG. 1(a), formed droplets suspended in a phosphorus-rich matrix. The micrograph of heat treated 43SG1 sample in FIG. 3(a) indicates that there is little tendency for these (crystallized) droplets to coalesce to form an interconnecting phase. By comparison, the micrographs of the 45SG1, 49SG1 wt % $SiO_2$ heat-treated samples (FIG. 3(b,c)) indicate that there is tendency for the microphases to form an interconnecting structure. Overall, the effect of heat treatment on interconnected phase can be explained as the formation, growth, and coalescence of the crystalline particles. See, e.g. T. H. Elemer, M. E. Nordberg, G. B. Carrier and E. J. Korda, "Phase Separation in Borosilicate Glasses as Seen by Electron Microscopy," *J. Am. Ceram. Soc.* 53, 171-75 (1970).

Figure 4:
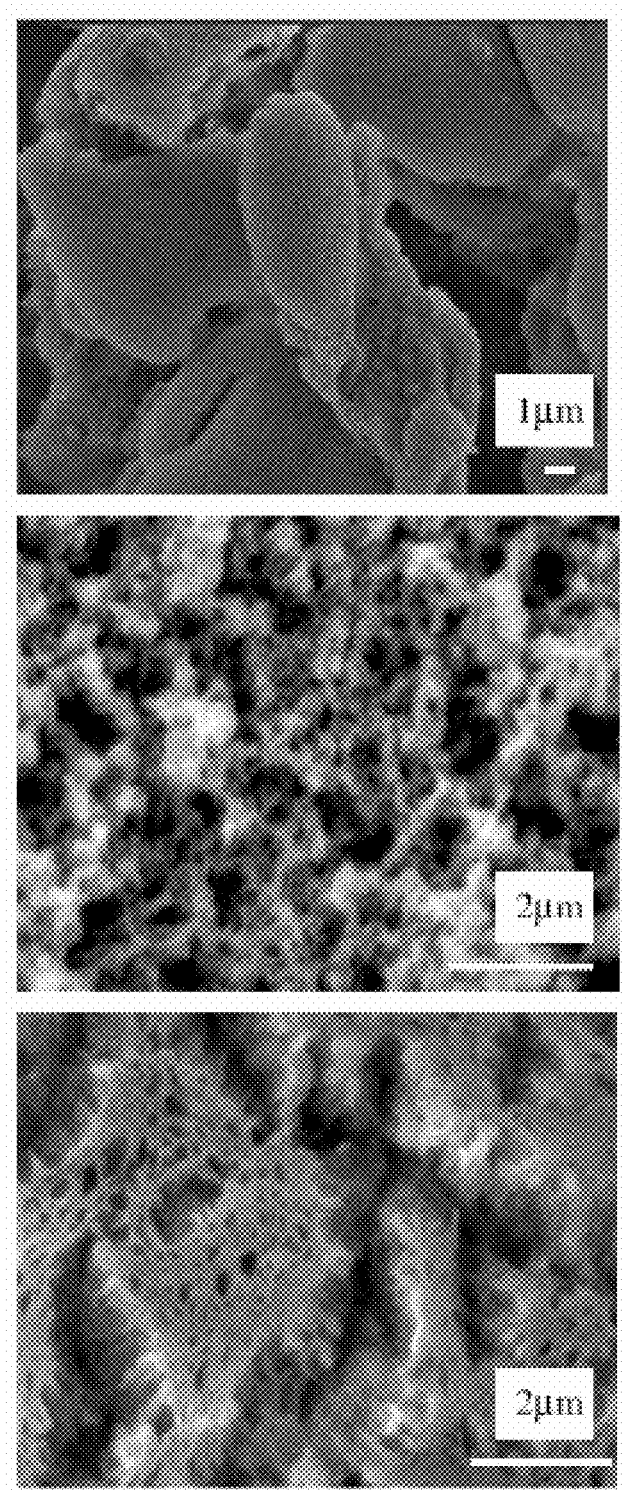
FIG. 4 illustrates SEM micrographs of the specimens after heat treatment and chemical leaching in 1N HCl: (a) 45SG1, (b) 47SG1, and (c) 49SG1.

FIG. 4 shows SEM micrographs of 45SG1, 47SG1, and 49SG1 glass-ceramic after the leaching chemical treatment.

Figure 5:
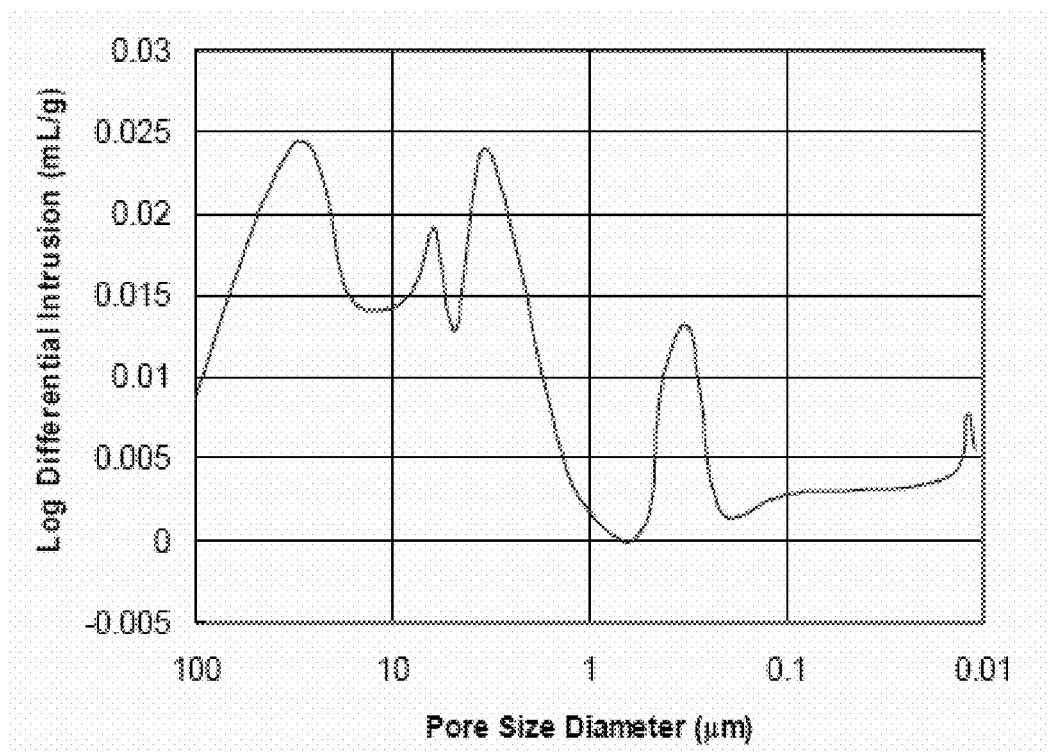
FIG. 5 illustrates pore size distribution in 49SG1 glass-ceramic after heat and chemical treatments.

The present melt-quench-heat-etch method has produced a structured porous network composed of interconnected nano/macroporosity. The multi-modal porosity includes interconnected nano/macroporosity in heat-and-chemical treated sample 49SG1, that result is confirmed by the mercury porosity data in FIG. 5, which shows a broad distribution of macropores with an average size of approximately 30 μm and additional distinct pores within the 0.1-8 μm range. On a much finer scale, the sample is further characterized by nanopores with average size of about 15 nm.

Figure 6:
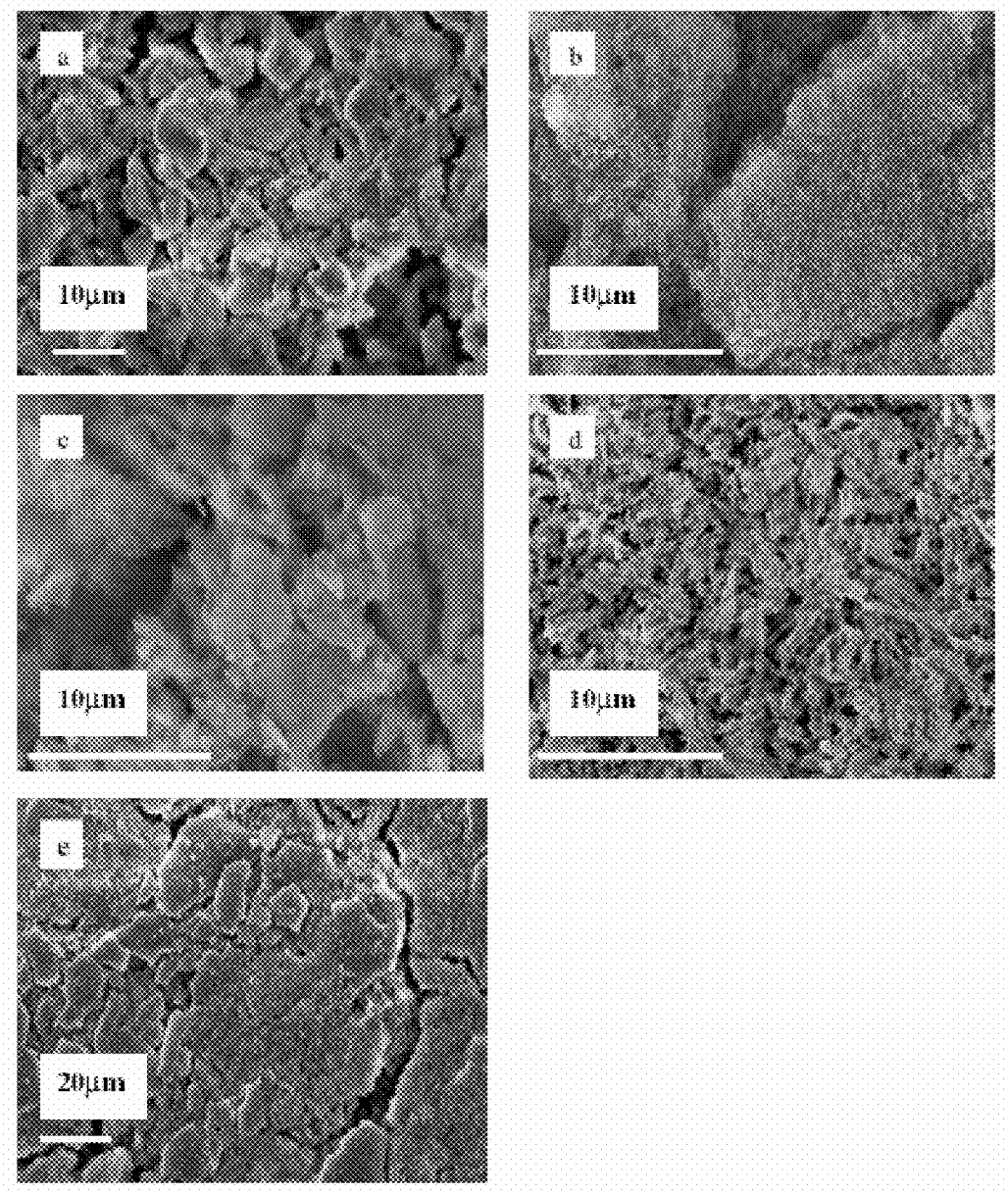
FIG. 6 illustrates SEM micrographs of specimens after soaking for 20 h in SBF: (a) 44SG1, (b) 45SG1, (c) 47SG1, (d) 49SG1, and (e) 45SG3.
Figure 7:
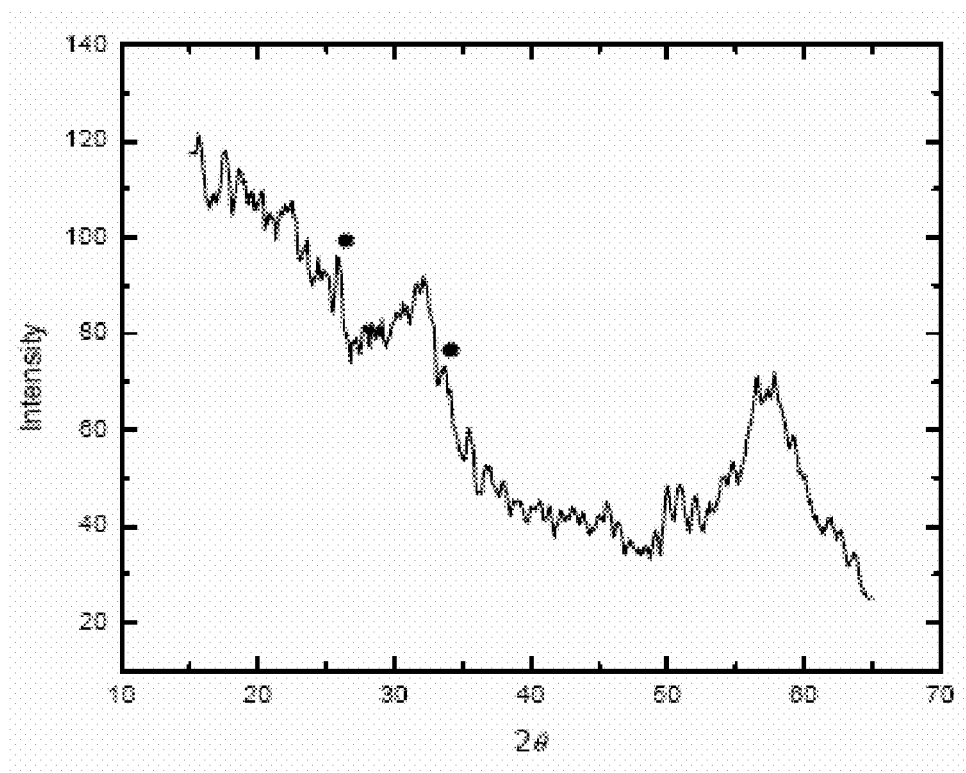
FIG. 7 illustrates the X-ray diffraction pattern of 45SG1 sample after soaking for 20 h in SBF. The marked peaks (•) correspond to those of crystalline HA.

FIG. 6 shows SEM micrographs of the glass-ceramic samples (44SG1, 45SG1, 47SG1, 49SG1, and 45SG3) after soaking in SBF for 20 h. Two layers with different compositions were formed on the surfaces of the samples. The first layer from the top covers the whole outer surface with HA and is enriched in Ca and P. The HA layer formed on the surface of the 45SG1 sample is identified by XRD pattern, as shown in FIG. 7, where the location of marked diffraction peaks matches with the main peaks of HA mentioned in PDF card number 09-0432 and is similar to that found by Peital et al. O. Peitl, E. D. Zanotto and L. L. Hench, "Highly Bioactive $P_2O_5$—$Na_2O$—$CaO$—$SiO_2$ Glass Ceramics," *J. Non-Cryst. Solids* 292, 115-26 (2001). Deposited particles aggregated in the large pores of samples 45SG1-47SG1, FIG. 6(*b, c*), while small particle aggregation appeared on the surface of 44SG1 and 49SG1 samples, see FIG. 6(*a, d*). FIG. 6(*b, e*) shows the top layer, HA, covering the whole surface of 45SG1, 45SG3 glass samples that were subjected to the crystal growth treatment for 6 h and 9 h, respectively, at 750° C. followed by chemical leaching. The thickness of top layer on the surface of 45S heat treated for 9 h (FIG. 6(*e*)) was significantly larger than that on the surface of sample heat treated for 6 h (FIG. 6(*b*)).

These results indicate that crystallization enhances HA formation. Comparing the formation of top layer on the surface of 44SG1-49SG1 glass-ceramics, we observe the influence of the initial composition, and hence the different phases and the multimodal porosity. See FIGS. 5 and 6. It appears that the multi-modal porosity characteristic of samples 44SG1-49SG1 allows the SBF to infiltrate the material freely and permits a more efficient transport of ions to and from the reactive surface during the 20 h soak.

The present heat treatment of 45S and 49S glasses exhibits a highly interconnected microstructure. This tendency of interconnected structure of these glasses is due to the growth and coalescence of the crystalline particles. By comparison, the 43S composition exhibits less interconnectivity after the effect of heat treatment.

There is significant effect of microstructure and crystallization-leaching process on apatite-layer formation on the surface of soda-lime phosphosilicate 44S-49S glass-ceramics that were synthesized by the melt-quench method. Testing in SBF showed the formation HA on the surface of 44S-49S glass-ceramics after soaking for 20 h, suggesting their good bioactivity. The formation of HA, and hence bioactivity, is influenced by the initial composition and the presence of the different phases that are produced by the thermal and chemical treatments described herein.

Accordingly, we have shown that the nominal 45S bioactive glass prepared by the melt-quench methods described herein is phase separated with an interconnected spinodal microstructure. Upon suitable heat treatment, the glass crystallizes into two Na—Ca silicate phases and a Ca phosphate phase, which are also interconnected in the resulting glass-ceramic composition. When the resulting bioactive glass-ceramic is treated with 1N HCl, these phases are selectively and partially leached out, resulting in multi-modal porosity characterized by an interconnected nano/macroporous structure.

Example 2

45S bioactive glass was prepared by melting a batch as described in Example 1 to make the 24.4% $Na_2O$-26.9% $CaO$-2.6% $P2O5$-46.1% $SiO_2$ (mol %) composition in a platinum crucible at 1500° C. for 2 h. The resulting homogenized melt was poured onto a stainless steel mold and then annealed at 520° C. to remove the residual stresses. The result was a glass phase separated by spinodal decomposition. To induce additional multiple phase separation, the sample was subjected further to a crystallization heat treatment in two steps: (a) nucleation at $T_n$, which consisted of heating at 3° C./min to 670° C. and holding there for 1 h, followed by (b) crystal growth at $T_x$, which included heating at the same rate to 750° C. and holding there for 6 h. To create the nano/macroporous 45S glass, the heat-treated sample was leached for 1 h in 1N HCl at 85° C. using 50 mL acid per gram of glass.

The pore size distribution of the resulting samples was determined by a mercury porosimeter (Micrometrics Auto Pore IV, Micromeritics Instrument Corporation, Norcross, Ga.). To identify the multiple phases and microstructure, the samples were analyzed by the X-ray diffraction technique and scanning electron microscopy.

Figure 8:
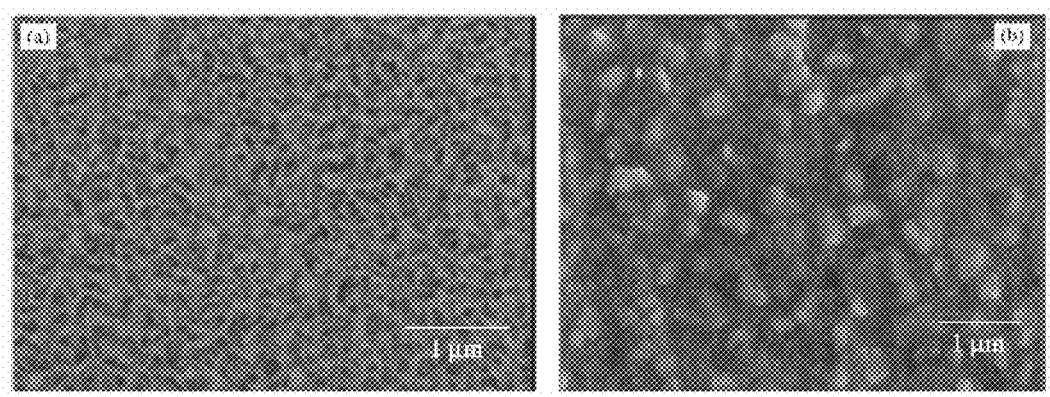
FIG. 8 illustrates SEM micrographs for (a) 45S as-prepared and (b) 45S after crystallization heat treatment at $T_n=670°$ C. for 1 h and $T_x=750°$ C. for 6 h.

FIG. 8(*a*) shows the microstructure of an as-prepared sample of the 45S glass, where spinodal decomposition is evidenced by a typical interconnected phase distribution. The phase separation in the glass appears to result from the presence of phosphorus ions ($P^{5+}$), which enter the glass structure tetrahedrally. See, e.g. F. H. Lin and M. H. Hon, "A Study on Bioglass Ceramics in The $Na_2O$—$CaO$—$SiO_2$—$P_2O_5$ System," *J. Mater. Sci.* 23, 4295-99 (1988). The charge difference between the principal network-forming $Si^{4+}$ and $P^{5+}$ cations leads to phase separation. Therefore, to satisfy electroneutrality, one of the phosphorus-oxygen bonds in tetrahedral $PO_4$ must be a double bond. The presence of this double-bonded oxygen within the silicate network creates a condition favoring separation into a phosphate-rich phase and a silicate-rich phase. Apparently, the spinodal structure provides nucleation sites for the subsequent crystallization of 45S glass.

The XRD pattern of the as-prepared glass confirmed that the phase-separated glass of FIG. 8(*a*) is completely amorphous. After the sample was subjected to a two-step heat treatment, the phase-separated structure gradually devitrified, as shown in FIG. 8(*b*). The XRD pattern of the heat-treated 45S5 sample showed the presence of three crystalline phases: two soda-lime silicate crystalline phases, $Na_2Ca_2Si_3O_9$ and $Na_2CaSi_3O_8$ (powder diffraction file ("PDF") card numbers #1-1078 and 12-671, respectively), and a calcium phosphate phase, $Ca_4P_6O_{19}$ (PDF #15-177). O. P. Filho, G. P. LaTorre, and L. L. Hench, "Effect of Crystallization on Apatite-Layer Formation of Bioactive Glass 45S5," *J. Biomed. Mater. Res.* 30, 509-14 (1996); O. Peitl, E. D. Zanotto, and L. L. Hench, "Highly Bioactive $P_2O_5$—$Na_2O$—$CaO$—$SiO_2$ Glass-Ceramics," *J. Non-Cryst. Solids* 292, 115-26 (2001). The main crystalline phases, $Na_2Ca_2Si_3O_9$ and $Na_2CaSi_3O_8$, assume a granular morphology with size around 0.6-0.9 μm, in addition to fine granular microcrystals of $Ca_4P_6O_{19}$. Heat treatment of the as-prepared 45S bioactive glass resulted in the coarsening of an already phase-separated glass structure, as well as crystallization of these phases. Accordingly, the phase-separated glass was heat treated to produce a crystallized glass-ceramic material.

Figure 9:
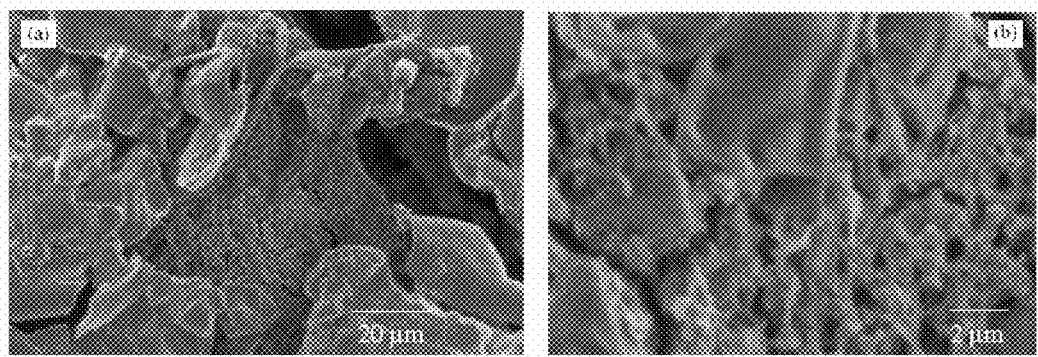
FIG. 9 illustrates SEM micrographs for bioactive glass-ceramic 45S after heat and chemical treatments in 1N HCl at (a) low magnification and (b) high magnification.
Figure 10:
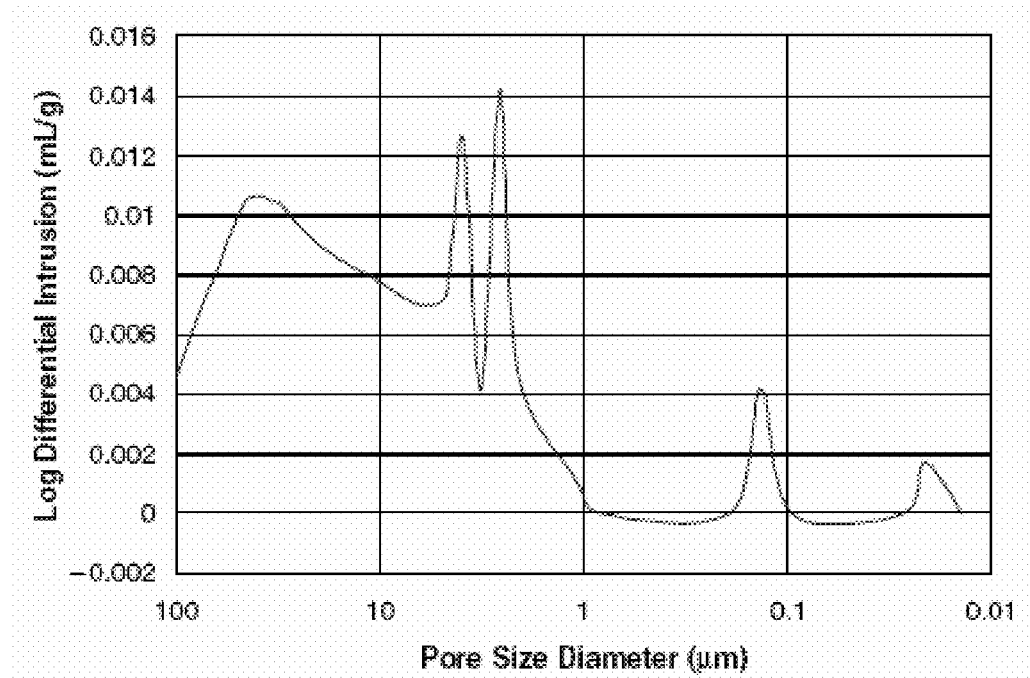
FIG. 10 illustrates pore size distribution in 45S glass-ceramic after heat and chemical treatments.

When the resulting 45S5 heat-treated glass-ceramic was placed in 1N HCl, the phases started leaching selectively, resulting in nano/macroporous interconnectivity as seen in FIG. 9. At a lower magnification, the photograph shows approximately 30 μm (or larger) pore structure (FIG. 9(a)). The same sample at a higher magnification shows the coexistence of 200 nm (or smaller) size pores (FIG. 9(b)). The multi-modal interconnected nano/macroporosity in this heat- and chemical-treated sample was confirmed by mercury porosity data in FIG. 10, which shows that the median size of the macropores is about 32 μm with additional distinct pores within the 0.1-8 μm range. On a much finer scale, the sample is characterized by nanopores having an average diameter of approximately 15 nm. The leaching process effectively removes parts of the sodium-calcium silicate and calcium phosphate phases; leaving behind a novel multi-modal glass-ceramic characterized by an interconnected nano/macroporous structure that remains biocompatible.

Qualitatively, the present samples appear to be stronger than similar compositions prepared by sol-gel methods. Furthermore, without limitation as to the theory, it appears that the optimum leaching process avoids complete leaching of either phase, thereby retaining sufficient fraction of these phases, which are needed for desirable levels of biological functionality. By contrast, in the Vycor® process (VYCOR® is a registered trademark of Corning, Inc., Corning, N.Y.), the acid completely leaches away the soda-rich phase resulting in only nanoporosity.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A method of making a nano/macroporous material comprising steps of: providing a composition comprising phase-separated, partly crystallized glass comprising an amorphous phase-separated microstructure; and leaching the phase-separated, partly crystallized glass with a leaching solution to thereby produce a nano/macroporous material, wherein the phase-separated, partly crystallized glass comprises CaO—$Na_2O$—$P_2O_5$—$SiO_2$.

2. A method of making a nano/macroporous material comprising steps of: providing a composition comprising phase-separated, partly crystallized glass comprising an amorphous phase-separated microstructure;

and leaching the phase-separated, partly crystallized glass with a leaching solution to thereby produce a nano/macroporous material, wherein the step of providing a composition comprising phase-separated, partly crystallized glass comprises the steps of: melting a mixture comprising $SiO_2$, $CaCO_3$, $NaCO_3$, and $Ca_5(OH)(PO_4)_3$ at a melting temperature for a first time period; and annealing the mixture at a reduced temperature for a second time period.

3. The method according to claim 2, further comprising steps of: heating the mixture to a nucleation temperature (Tn) for a third time period; and thereafter heating the product of the previous step to a crystal growth temperature (Tx) for a fourth time period.

4. The method according to claim 2, wherein the melting temperature is about 1400° C. or greater and the first time period is about 1 h or longer.

5. The method according to claim 2, wherein the reduced temperature is about 500° C. and the second time period is about 1 h or longer.

6. The method according to claim 3, wherein the nucleation temperature is about 670° C. and the third time period is about 1 h or longer.

7. The method according to claim 3, wherein the crystal growth temperature is about 700° C. to about 1100° C.

8. The method according to claim 3, wherein the crystal growth temperature is about 750° C. to about 1075° C.

9. The method according to claim 3, wherein the fourth time period is about 3 h or longer.

10. The method according to claim 3, wherein the fourth time period is about 6 h to about 9 h.

11. The method according to claim 2, wherein the leaching solution has a pH of less than 7 and comprises an inorganic mineral acid.

12. The method according to claim 2, wherein the leaching solution is a 1N HCl solution.

13. The method according to claim 2, wherein the leaching step is carried out for about 1 h in 1N HCl at about 85° C. using about 50 mL acid per gram of glass.

* * * * *